US008808351B2

(12) United States Patent
Osborne

(10) Patent No.: US 8,808,351 B2
(45) Date of Patent: *Aug. 19, 2014

(54) STRETCHABLE PROSTHESIS FENESTRATION

(75) Inventor: Thomas A. Osborne, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 434 days.

This patent is subject to a terminal disclaimer.

(21) Appl. No.: 10/962,632

(22) Filed: Oct. 12, 2004

(65) Prior Publication Data

US 2005/0102021 A1   May 12, 2005

Related U.S. Application Data

(60) Provisional application No. 60/510,243, filed on Oct. 10, 2003.

(51) Int. Cl.
*A61F 2/06* (2013.01)

(52) U.S. Cl.
USPC ........................................................ 623/1.13

(58) Field of Classification Search
USPC .................... 623/1.32, 1.35, 1.13, 1.15, 1.26; 606/157
See application file for complete search history.

(56) References Cited

U.S. PATENT DOCUMENTS

| | | | | |
|---|---|---|---|---|
| 1,597,525 A | * | 8/1926 | Knake | 411/540 |
| 3,553,796 A | * | 1/1971 | Carlile | 24/689 |
| 4,040,697 A | * | 8/1977 | Ramsay et al. | 439/268 |
| 5,366,473 A | * | 11/1994 | Winston et al. | 606/198 |
| 5,603,698 A | * | 2/1997 | Roberts et al. | 604/104 |
| 5,653,743 A | * | 8/1997 | Martin | 623/1.35 |
| 5,662,703 A | * | 9/1997 | Yurek et al. | 623/1.12 |
| 5,676,697 A | * | 10/1997 | McDonald | 623/1.35 |
| 5,843,766 A | * | 12/1998 | Applegate et al. | 435/284.1 |
| 5,961,548 A | * | 10/1999 | Shmulewitz | 623/1.35 |
| 5,984,955 A | * | 11/1999 | Wisselink | 623/1.35 |
| 6,086,526 A | * | 7/2000 | Francischelli | 600/16 |
| 6,344,052 B1 | * | 2/2002 | Greenan et al. | 623/1.1 |
| 6,395,018 B1 | * | 5/2002 | Castaneda | 623/1.13 |
| 7,413,573 B2 | * | 8/2008 | Hartley et al. | 623/1.13 |
| 2001/0044647 A1 | * | 11/2001 | Pinchuk et al. | 623/1.13 |
| 2002/0052648 A1 | * | 5/2002 | McGuckin et al. | 623/1.35 |
| 2004/0015232 A1 | * | 1/2004 | Shu et al. | 623/2.4 |
| 2004/0034406 A1 | * | 2/2004 | Thramann | 623/1.13 |

(Continued)

FOREIGN PATENT DOCUMENTS

AU         WO 9929262       *  6/1999   ............... A61F 2/06

OTHER PUBLICATIONS

Branched and Fenestrated Stent-Grafts presentation, Tim Chuter, MD, 15 pages.
Branched Stent-Grafts presentation, Tim Chuter, MD, 24 pages.

(Continued)

*Primary Examiner* — Thomas McEvoy
(74) *Attorney, Agent, or Firm* — Brinks Gilson & Lione

(57) ABSTRACT

A prosthesis (10) having a variable size or stretchable fenestration (14) in the graft material (37) of a biocompatible tubular graft (11). An expandable frame (16) is disposed about the fenestration, and a portion (17) of the graft material about the fenestration is folded back over the frame to cover the frame. Additional grafts or prosthesis of varying size can be inserted through the frame and fenestration with the stretched frame and folded portion compressing on the inserted graft forming a seal therewith.

24 Claims, 6 Drawing Sheets

(56) References Cited

U.S. PATENT DOCUMENTS

| | | | |
|---|---|---|---|
| 2004/0059406 A1* | 3/2004 | Cully et al. | 623/1.11 |
| 2004/0122504 A1* | 6/2004 | Hogendijk | 623/1.15 |
| 2004/0258502 A1* | 12/2004 | Unsworth et al. | 411/412 |
| 2007/0162105 A1* | 7/2007 | Molaei | 623/1.18 |

OTHER PUBLICATIONS

Branched Stent-Grafts presentation, Tim Chuter, MD, 2002, 30 pages.

Branched Stent-Grafts presentation, Tim Chuter, MD, 29 pages.

Endovascular AAA Repair presentation, Tim Chuter, MD, 2002, 56 pages.

Endovascular AAA Repair presentation, Tim Chuter, MD, 2002, 44 pages.

Endovascular AAA Repair presentation, Tim Chuter, MD, Division of Vascular Surgery, University of California San Francisco, updated Sep. 2002, Part 1—50 pgs. and Part 2—44pgs.

* cited by examiner

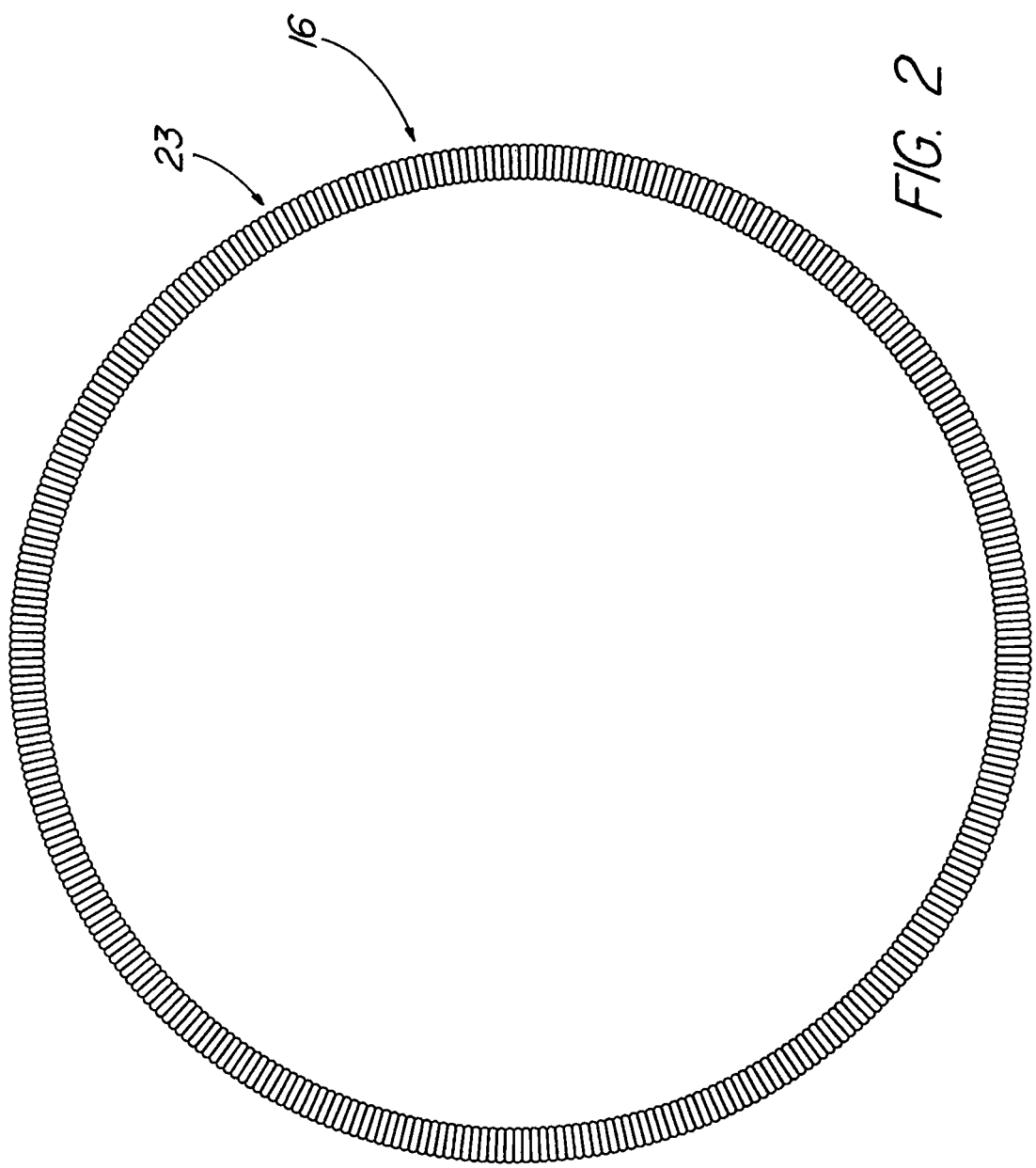

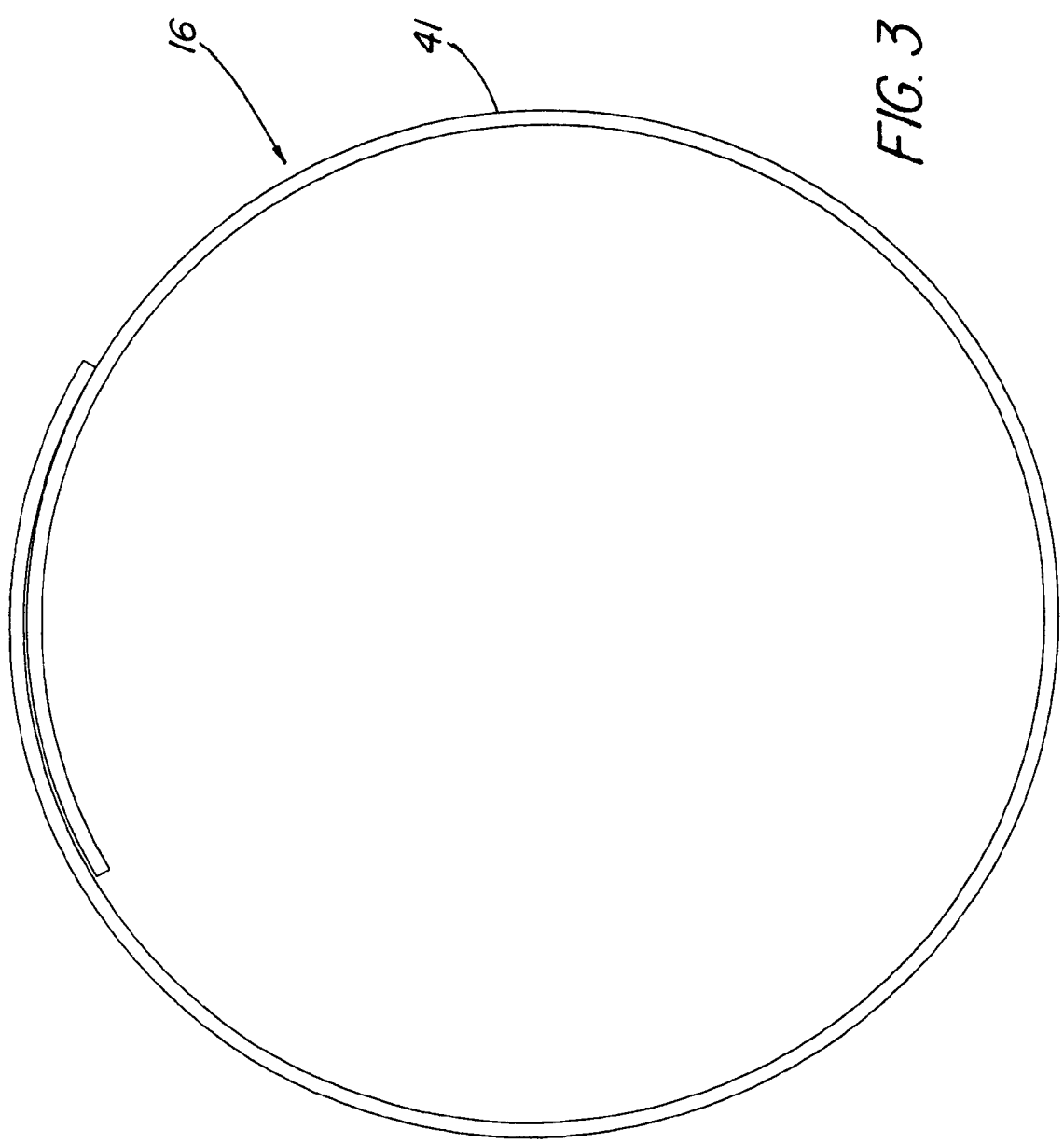

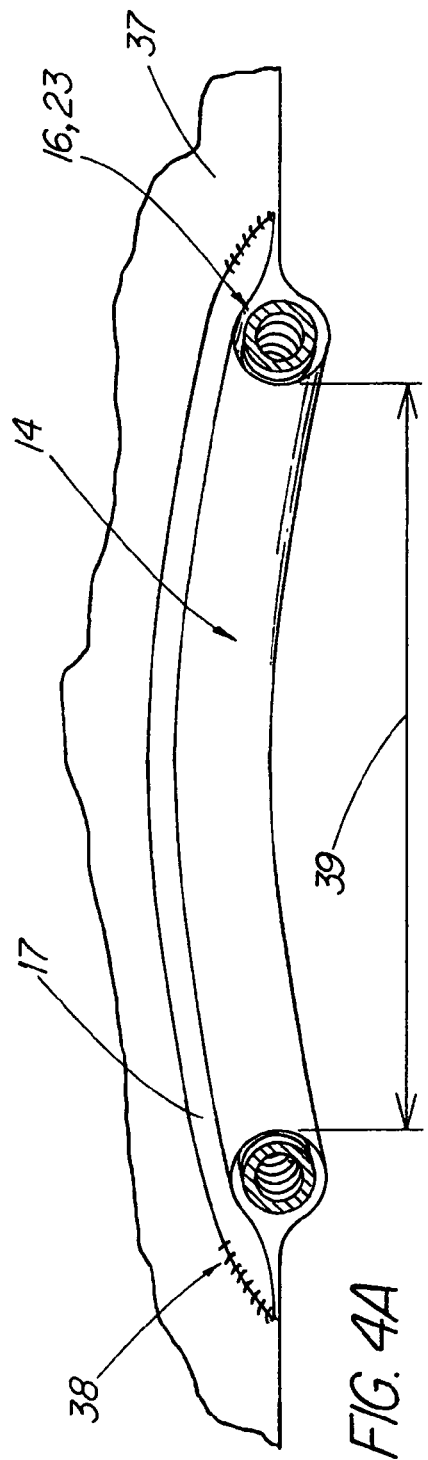
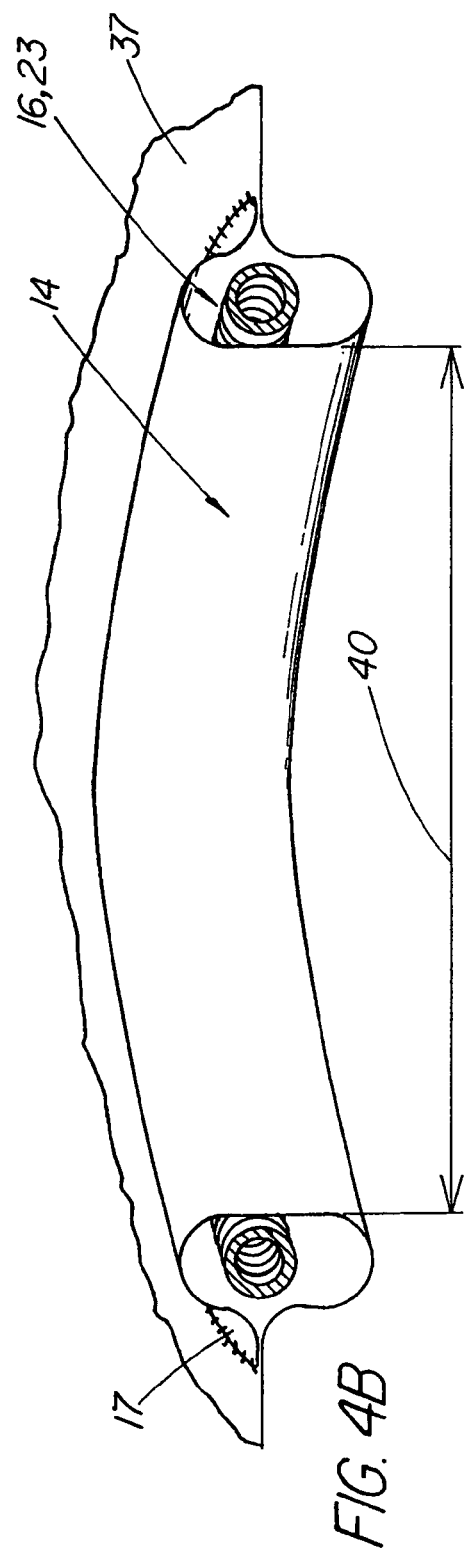

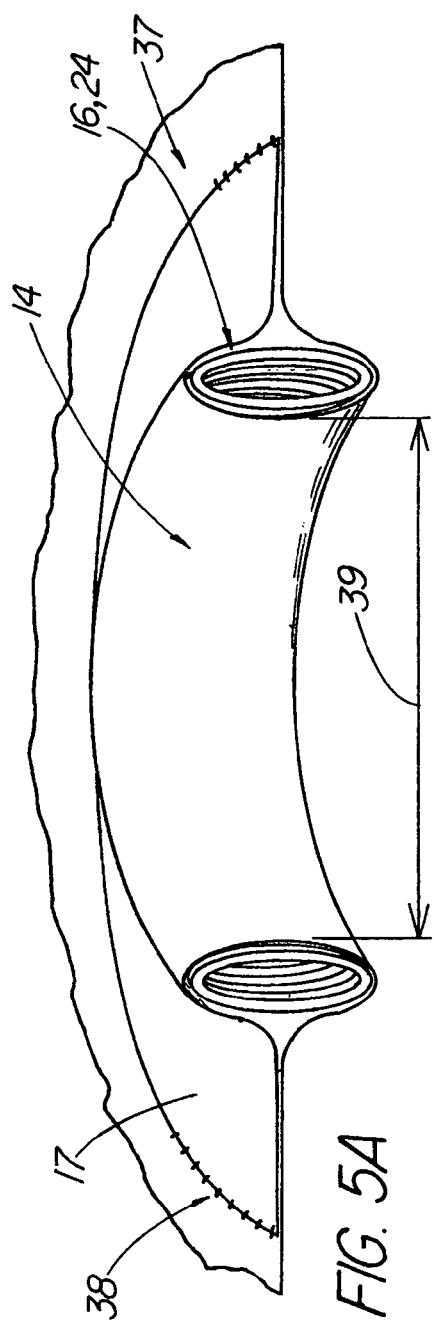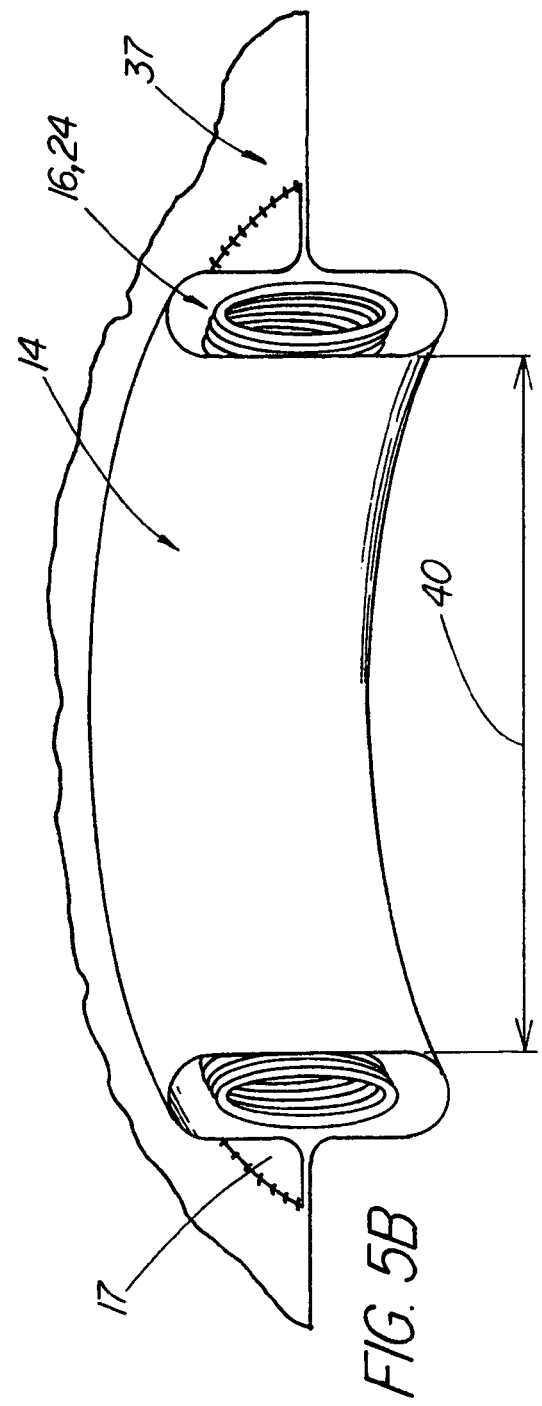
FIG. 5A
FIG. 5B

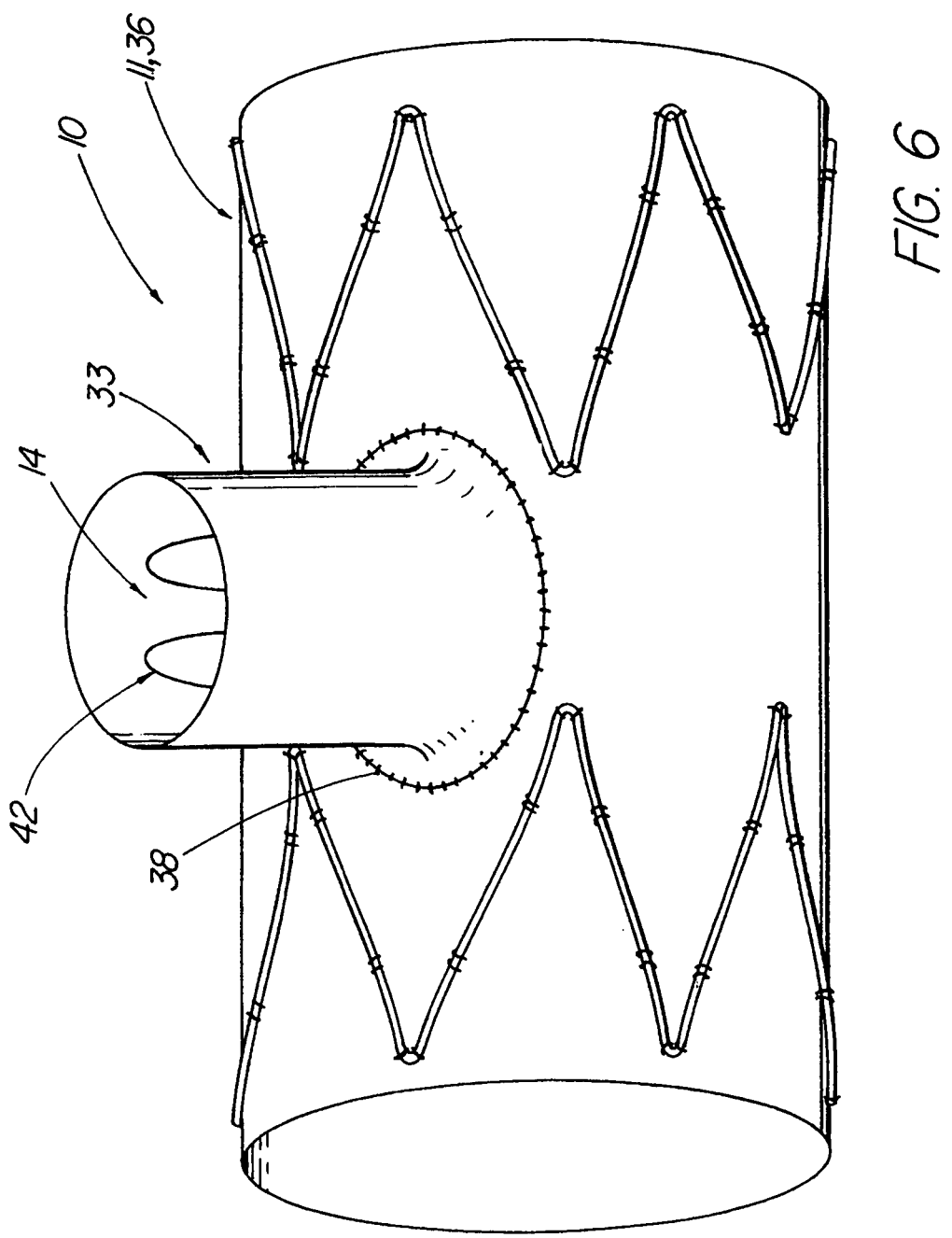

STRETCHABLE PROSTHESIS FENESTRATION

This application claims priority of provisional application Serial No. 60/510,243, filed Oct. 10, 2003.

TECHNICAL FIELD

This invention is related to medical devices and, in particular, to a prosthesis having a fenestration.

BACKGROUND OF THE INVENTION

Prostheses such as stent grafts as used for stenting or repairing aneurysms as in the abdominal or thoracic aorta are usually fairly effective at excluding the aneurysm from exposure to blood pressure and therefore protect the patient from the dangers of aneurysm rupture. However, these stent grafts frequently block the flow of blood to the side branch vessels that carry blood to other organs and anatomy. The occlusion of the side branch vessels can result in damage to the tissue perfused by the blood flow from the side branch vessel.

Attempts to deal with these occlusions have been such things as by-pass vessels placed surgically to restore blood flow from a region of the aorta that is not stented and the placement of holes or fenestrations in the stent grafts that are aligned with the side branch vessel so as to allow blood to continue to flow into the side branch vessel. The fenestration approach is the preferred method since it does not involve major vascular surgery. Patients receiving stent grafts usually do so because they are too weak or sick to endure surgery. Once the fenestrated stent graft is deployed, the stent graft is anchored to the ostium of the side branch with a balloon expanded stent. This stent is placed so that the bulk of the stent length is in the side branch with 1 or 2 mm extending into the lumen of the stent graft. The 1 or 2 mm segment is then over expanded, or flared slightly, to hold the stent graft to the aortic wall and effect a seal that prevents blood from flowing into the aneurysm.

While this balloon stenting through a fenestration process is fairly effective, it is deficient in that the connection between the balloon expanded stent and the stent graft at the fenestration is never completely snug or tight. As a result, leaks often occur between the stent graft and aortic wall. The reason this connection can never truly be a tight, zero clearance fit is because balloon expandable stents always have some amount of recoil after they are expanded by the delivery balloon. This recoil is usually 4% to 10% of the stent diameter attained prior to balloon deflation. As a result, the fit between the balloon expandable stent and the stent graft fenestration is never truly tight. The eventual endothelialization of the area around the fenestration and the ostium or origin of the side branch is the only hope of an eventual complete seal and exclusion of the aneurysm. Before endothelialization occurs, the patient is still at risk of a ruptured aneurysm. In some cases, where the gap between the stent graft and aortic wall is large, a seal at the fenestration may never occur, leaving the patient with minimal or no protection from a ruptured aneurysm.

Other exemplary prostheses including stents, grafts, and stent grafts with, for example, fenestrations are disclosed in U.S. Pat. Nos. 6,524,335; 5,984,955; 6,395,018; 6,325,826; 6,077,296; 6,030,414; 5,617,878; 5,425,765; and 4,580,569, all of which are incorporated herein by reference in their entirety.

SUMMARY OF THE INVENTION

The foregoing problems are solved and a technical advance is achieved in an illustrative embodiment of a stretchable prosthesis fenestration including a variable size fenestration in the stent graft of the present invention. This invention provides a variable size fenestration or hole in the stent, graft or stent graft that is stretchable or elastic. By being stretchable, a balloon expandable stent can be advantageously expanded beyond the diameter of the fenestration without damaging the stent, graft or stent graft and will recoil along with the balloon expanded stent and maintain a close, snug fit to it. An expandable frame is disposed at least partially about the fenestration and at least partially controls the variable size of the fenestration to advantageously accommodate a close or snug fit with another prosthesis such as a stent, graft or stent graft positioned therethrough.

BRIEF DESCRIPTION OF THE DRAWING

FIG. 2 shows a stretchable fenestration frame of the present invention made from coil spring material;

FIG. 3 shows an expandable fenestration frame of the present invention made from solid wire;

FIGS. 4A and 4B depict cross sectional views through the stretchable fenestration of the present invention using the coil spring frame in the relaxed and stretched conditions;

FIGS. 5A and 5B depict cross sectional views of another stretchable fenestration frame of the present invention where the coil frame is an oval or flat coil spring in the relaxed and stretched conditions; and FIG. 6 depicts the stent graft of the present invention with a side branch graft connected to the main graft and fenestration;

DETAILED DESCRIPTION

Figure 1:
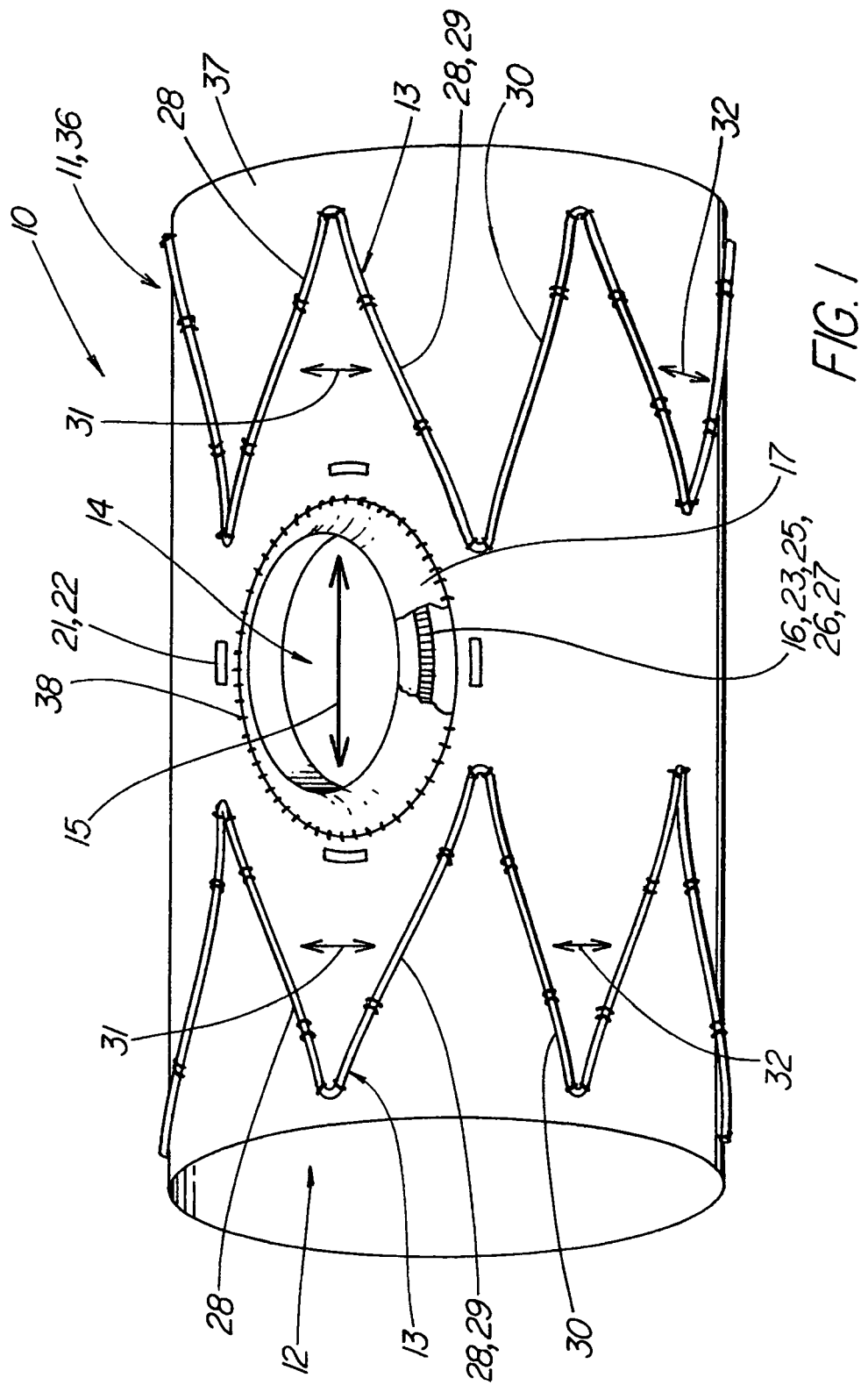
FIG. 1 shows a segment of stent graft with a fenestration of the present invention.

FIG. 1 depicts a pictorial view of a segment of an illustrative prosthesis 10 such as a stent graft of the present invention in which a variable size fenestration 14 is disposed in tubular graft 11, 36. Biocompatible tubular graft 11 or elongated tubular member 36 of graft material 37 includes a lumen 12 extending longitudinally therethrough.

The fenestration 14 can be made by first cutting a round hole in the graft material 37 that is considerably smaller than the desired finished hole. An expandable frame 16 such as a stretchable coil loop 23 as in FIG. 2 is laid on the graft material, around the hole, then the graft material is everted through the coil loop and out over the loop back onto the graft material. The edge can then be sutured or sewn to the graft material using well-known sutures 38 and capturing the coil loop at the resulting hole or fenestration. The result is prosthesis 10, tubular graft 11, or elongated tubular member 36 depicted in FIG. 1. A tubular graft sleeve can also be positioned and attached to the hole to facilitate the eversion or fold back.

The folded portion 17 of the graft that is everted through the coil frame and back out onto the graft material needs to be stitched far enough away from the coil frame so as to allow a space for the coil frame to expand. The variable size 15 of the fenestration 14 is depicted in FIGS. 4A, 4B, 5A, and 5B. FIGS. 4A, 4B, 5A, and 5B illustrate how variable size 15 of the opening or fenestration 14 expands as the coil loop frame is stretched. Diameter 39 is the relaxed, un-stretched diameter, and diameter 40 is the maximum stretched or expanded diameter. From the diameter 40 or the expanded diameter, the coil loop frame will cause the fenestration to be tight or snug around the stent that is positioned through the fenestration and into the side branch artery.

The coil loop shown in FIGS. 5A and 5B is an alternative form of the coil loop frame. The coil from which the loop is made is made in an oval shape 24. This will result in a fenestration that has a flange or protrusion that will seat in the ostium of the side branch vessel and improve the seal between the stent graft and aorta. The oval shaped coil will also increase the amount of surface area in contact with a balloon expandable stent or stent graft, further improving the seal between the stent graft and aorta.

FIG. 3 shows an alternate form of fenestration frame 16 that uses a solid wire frame 41. It is simply a loop wherein the ends overlap. The overlap portion allows the loop to expand and contract a small amount. The expansion and contraction allows the fenestration to expand as needed when the balloon expandable stent is expanded in it and contract with the balloon expanded stent as the balloon is deflated, thus maintaining a tight fit to the balloon expanded stent.

The materials used to make the fenestration frames can be any springy, biocompatible material, such as stainless steel, nitinol, Elgiloy, MP35N, platinum and many other materials including polymers. Platinum would have the added advantage of providing improved radiopacity of the fenestration, making it easier for the physician to accurately place the fenestration in the side branch vessel.

In addition to the wire and spring fenestration loops described, it is also possible to make stretchable fenestration frames using elastic bands, such as Silicone rubber "O" rings 25, or any other biocompatible elastomer 26.

In addition to using the radiopacity of the fenestration frame to aid in the placement and orientation of the stent graft, separate radiopaque markers 21 can be added to the stent graft as depicted in FIG. 1 in the vicinity of or around the periphery of the fenestration. These markers can be radiopaque material 22 such as gold, platinum, tungsten, and any other high density material 27 such bands or wires and can be shaped and/or oriented in such a way so as to indicate rotational orientation fluoroscopically.

The size of a fenestration can typically vary over a range of about 2 to 10 mm diameter. The wire used to make the coil frames would be in the 0.002 to 0.006 in. diameter range. Flat, square, rectangular and oval wire could also be used to make the coil loop frames 16. The diameter of the coil in the coil loop frame would be in the 0.010 to 0.050 in. range. The long and short axis of the oval coil loop frame would be in the 0.005×0.010 inch to 0.020×0.050 inch range. The long axis dimension could be greater if a longer or taller flange protrusion around the fenestration is desired. The wire in the wire loop frame could be in the 0.010 to 0.060 inch diameter range.

The coil loop frame 16 can be made by first coiling the wire to the desired coil diameter by any number of well known coil spring winding techniques and then joining the ends of a length of the coil to form a loop frame 23 of the desired diameter. The ends of the coil could be welded, soldered or glued together to form the continuous coil loop. The ends of the coil could also be stretched slightly over a distance of about 1 mm so that the two ends could be threaded or screwed together to form a mechanical connection. The oval coil loop 24 can be made in much the same manner except that the original coil would be pressed or flattened to form the short diameter of the oval.

The shape of stents 13 used to make the stent graft could be altered to accommodate the inclusion of the fenestrations and frames. For example, the most common stent in a stent graft is the Gianturco "Z" stent (U.S. Pat. No. 4,580,568). The straight struts 28 of the Z stent that are adjacent to the fenestration could be curved as depicted in FIG. 1 so that a larger space is provided for the fenestration. The Z stents can also just be spaced far enough apart as with strut spacing 31 as opposed to lesser spacing 32 so as to allow the formation of a fenestration between them. The length 29 of the straight struts can also be reduced in the area of the fenestration as opposed to longer strut length so as to allow the stents to remain close together while providing a space for the fenestration.

In addition to a separate stretchable fenestration frame, a side branch graft 33 can be attached to the fenestrated area in the main stent graft that is made of a "stretch fabric," similar to the tops of stockings and the like that has an unstretched diameter smaller than the side branch vessel diameter that allows it to be easily maneuvered into the side branch, and then another stent 42 such as a Z stent is placed inside it that would stretch the side branch portion up to the diameter of the side branch vessel and create a long fluid tight seal between the side branch vessel and the main stent graft. This is depicted in FIG. 6.

The graft material can be any biocompatible material such as any biocompatible polymer such as Dacron, commercially available Thoralon™ material and the like and biological materials such as extracellular matrix (ECM) material, for example, small intestine submucosa (SIS) of porcine, bovine and the like. This ECM material is described and claimed in the patents of Purdue University and Cook Biotech, which are all incorporated by reference herein. This SIS and other ECM material is commercially available from Cook Biotech, West Lafayette, Ind.

The following list of figure elements is provided only for informational purposes and is not intended to limit the claims in any manner.

ELEMENT LIST 10. prosthesis
11. biocompatible tubular graft
12. lumen of 11
13. expandable stent
14. fenestration of 11
15. variable size of 14
16. expandable frame
17. folded portion of 11
18. second tubular graft
19. second lumen of 18
20. covered portion of 17
21. radiopaque marker
22. radiopaque material of 21
23. coil loop frame (round cross-sectional shape)
24. oval-shaped coil loop frame (oval cs shape)
25. 0-ring
26. silicone rubber and any other elastic polymer material of 25
27. gold, platinum, and any other high density material of 22
28. struts
29. first strut length
30. second strut length
31. first strut spacing
32. second strut spacing
33. side branch graft
34. internal to lumen 12
35. external to lumen 12
36. elongated tubular member
37. graft material
38. sutures
39. diameter (relaxed)
40. diameter (stretched)
41. solid wire frame (16)
42. branch stent

What is claimed is:

1. A prosthesis, comprising:
a biocompatible tubular graft having a lumen extending at least longitudinally therein, the lumen having a maximum diameter;
an expandable stent engageable with said graft, wherein said stent is capable of maintaining at least a portion of said lumen of said graft patent;
a fenestration disposed in the graft having a variable size and communicating with said lumen, and adapted to receive a branch graft, the fenestration having a maximum diameter less than the maximum diameter of the lumen; and,
a radially elastic frame comprising a single wire having overlapping ends disposed at least partially about said fenestration, and at least partially controlling the variable size of said fenestration;
where the diameter of the frame elastically expands in response to the application of a mechanical expanding force and contracts upon removal of the expanding force to maintain a fluid tight seal with the branch graft.

2. The prosthesis of claim 1, wherein said graft includes a folded portion at least partially adjacent said fenestration and greater in size than said fenestration.

3. The prosthesis of claim 2, wherein said folded portion at least partially covers said expandable frame and wherein said folded portion is disposed over said expandable frame and includes a covered portion to allow said expandable frame to vary the size of said fenestration.

4. The prosthesis of claim 1, wherein said variable size preferably ranges from 1 to 15 millimeters, and wherein said expandable frame ranges in size less than the size of said fenestration.

5. The prosthesis of claim 1, further comprising at least one radiopaque marker disposed about said fenestration.

6. The prosthesis of claim 5, wherein the at least one radiopaque marker is composed of high density material.

7. The prosthesis of claim 6, wherein said high density material is gold or platinum.

8. The prosthesis of claim 1, wherein said expandable frame comprises a coil loop frame or an oval-shaped coil loop frame.

9. The prosthesis of claim 1, wherein said expandable stent includes struts having at least two different lengths and wherein said struts have variable spacing therebetween.

10. The prosthesis of claim 1, wherein said fenestration includes a side branch graft extending therefrom either internal or external to said lumen.

11. A prosthesis comprising:
an elongated tubular member including at least one of a graft and a stent having a lumen extending at least longitudinally therein, the lumen having a maximum diameter;
where said tubular member includes a fenestration disposed in the tubular member, said fenestration having a variable size and communicating with said lumen, and adapted to receive a branch graft, the fenestration having a maximum diameter less than the maximum diameter of the lumen; and,
a radially elastic frame comprising a single wire having overlapping ends disposed at least partially about said fenestration, and at least partially controlling the variable size of said fenestration;
where the diameter of the frame elastically expands in response to the application of a mechanical expanding force and contracts upon removal of the expanding force to maintain a fluid tight seal with the branch graft.

12. The prosthesis of claim 11, wherein said graft includes a folded portion at least partially adjacent said fenestration and greater in size than said fenestration.

13. The prosthesis of claim 12, wherein said folded portion at least partially covers said expandable frame and wherein said folded portion is disposed over said expandable frame and includes a covered portion to allow said expandable frame to vary the size of said fenestration.

14. The prosthesis of claim 11, wherein said variable size preferably ranges from 1 to 15 millimeters, and wherein said expandable frame ranges in size less than the size of said fenestration.

15. The prosthesis of claim 11, wherein said expandable frame comprises a coil loop frame or an oval-shaped coil loop frame.

16. The prosthesis of claim 15, wherein said fenestration includes a side branch graft extending therefrom either internal or external to said lumen.

17. The prosthesis of claim 11, further comprising at least one radiopaque marker disposed about said fenestration.

18. The prosthesis of claim 17, wherein the at least one radiopaque marker is composed of high density material.

19. The prosthesis of claim 18, wherein said high density material is gold or platinum.

20. The prosthesis of claim 11, wherein said expandable stent includes struts having at least two different lengths and wherein said struts has variable spacing therebetween.

21. A prosthesis, comprising:
a biocompatible tubular graft having a lumen extending at least longitudinally therein, the lumen having a maximum diameter;
an expandable stent engageable with said graft, wherein said stent is capable of maintaining at least a portion of said lumen of said graft patent;
a fenestration disposed in the graft having a variable size and communicating with said lumen, and adapted to receive a branch graft, the fenestration having a maximum diameter less than the maximum diameter of the lumen; and,
an elastic frame comprising a single wire having overlapping ends disposed at least partially about said fenestration, and at least partially controlling the variable size of said fenestration;
where the diameter of the elastic frame radially increases in response to the application of a mechanical expanding force and spontaneously substantially contracts to its original shape upon the removal of the expanding force to maintain a tight fluid seal with the branch graft.

22. A prosthesis, comprising:
a biocompatible tubular graft having a lumen extending at least longitudinally therein, the lumen having a maximum diameter;
an expandable stent engageable with said graft, wherein said stent is capable of maintaining at least a portion of said lumen of said graft patent;
a fenestration disposed in the graft having a variable size and communicating with said lumen, and adapted to receive a branch graft, the fenestration having a diameter less than the maximum diameter of the lumen; and,
a radially elastic frame comprising a single wire having overlapping ends fastened to the graft about the circumference of the fenestration, and at least partially controlling the variable size of said fenestration;
where the diameter of the frame elastically expands about the periphery of the branch graft in response to the application of a mechanical expanding force and contracts upon removal of the expanding force to maintain a fluid tight seal between an internal surface of the frame and an external surface of the branch graft, and where the frame is separate from the expandable stent.

23. A prosthesis comprising:

an elongated tubular member including at least one of a graft and a stent having a lumen extending at least longitudinally therein, the lumen having a maximum diameter;

where said tubular member includes a fenestration disposed in the tubular member, said fenestration having a variable size and communicating with said lumen, and adapted to receive a branch graft, the fenestration having a maximum diameter less than the maximum diameter of the lumen; and, a radially elastic frame comprising a single wire having overlapping ends fastened to the graft about the circumference of the fenestration, and at least partially controlling the variable size of said fenestration;

where the diameter of the frame elastically expands about the periphery of the branch graft in response to the application of a mechanical expanding force and contracts upon removal of the expanding force to maintain a fluid tight seal between an internal surface of the frame and an external surface of the branch graft, and where the frame is separate from the expandable stent.

24. A prosthesis, comprising:

a biocompatible tubular graft having a lumen extending at least longitudinally therein, the lumen having a maximum diameter;

an expandable stent engageable with said graft, wherein said stent is capable of maintaining at least a portion of said lumen of said graft patent;

a fenestration disposed in the graft having a variable size and communicating with said lumen, and adapted to receive a branch graft, the fenestration having a maximum diameter less than the maximum diameter of the lumen; and, an elastic frame comprising a single wire having overlapping ends fastened to the graft about the circumference of the fenestration, and at least partially controlling the variable size of said fenestration;

where the diameter of the elastic frame radially increases about the periphery of the branch graft in response to the application of a mechanical expanding force and spontaneously contracts substantially to its original shape upon the removal of the expanding force to maintain a tight fluid seal between an internal surface of the frame and an external surface of the branch graft, and where the frame is separate from the expandable stent.

* * * * *